US008837832B2

(12) United States Patent
Kislal

(10) Patent No.: US 8,837,832 B2
(45) Date of Patent: Sep. 16, 2014

(54) SYSTEMS AND METHODS FOR MONITORING THE CONDITION OF THE SKIN

(75) Inventor: Ellen Eide Kislal, Tarrytown, NY (US)

(73) Assignee: Skin of Mine Dot Com, LLC, Valhalla, NY (US)

( * ) Notice: Subject to any disclaimer, the term of this patent is extended or adjusted under 35 U.S.C. 154(b) by 392 days.

(21) Appl. No.: 12/833,064

(22) Filed: Jul. 9, 2010

(65) Prior Publication Data
US 2011/0286643 A1    Nov. 24, 2011

Related U.S. Application Data

(60) Provisional application No. 61/345,886, filed on May 18, 2010.

(51) Int. Cl.
    *G06K 9/18*        (2006.01)
    *A61B 5/00*        (2006.01)
    *G06T 7/00*        (2006.01)

(52) U.S. Cl.
CPC ..... *G06T 7/0012* (2013.01); *G06T 2207/30088* (2013.01); *A61B 5/441* (2013.01)
USPC .......................................... 382/182; 382/190

(58) Field of Classification Search
CPC .......................... G06K 9/18; G06T 2207/10016
USPC .......................................... 382/128, 182, 190
See application file for complete search history.

(56) References Cited

U.S. PATENT DOCUMENTS

| | | | |
|---|---|---|---|
| 5,862,272 A | 1/1999 | Ishiguro | |
| 7,233,693 B2 | 6/2007 | Momma | |
| 7,564,990 B2 * | 7/2009 | Kern et al. | 382/100 |
| 8,064,677 B2 * | 11/2011 | Nie et al. | 382/132 |
| 2005/0226821 A1 | 10/2005 | Waugh | |
| 2007/0040907 A1 * | 2/2007 | Kern et al. | 348/77 |
| 2007/0053559 A1 * | 3/2007 | Corrion | 382/128 |
| 2007/0191741 A1 * | 8/2007 | Tsai et al. | 600/587 |
| 2009/0316168 A1 | 12/2009 | Enjuji | |
| 2010/0166331 A1 | 7/2010 | Chan | |
| 2010/0271470 A1 | 10/2010 | Stephan | |
| 2011/0002511 A1 * | 1/2011 | Imaoka | 382/118 |
| 2011/0262014 A1 | 10/2011 | Kuo | |

OTHER PUBLICATIONS

Carrara et al., Automated Segmentation of Pigmented Skin Lesions in Multispectral Imaging, Published on Nov. 2, 2005.*

* cited by examiner

*Primary Examiner* — Neha Patel
(74) *Attorney, Agent, or Firm* — Ference & Associates LLC

(57) ABSTRACT

Systems, methods, apparatuses and program products for analyzing and/or monitoring the condition of skin are provided. Various embodiments provide for accessing images of the skin, analyzing the characteristics of skin conditions as represented by the images, and providing outputs useful for analyzing and/or monitoring conditions of the skin. Certain embodiments provide for automated analysis of skin conditions such as moles and/or wrinkles. The automated analysis may include for example characterization of a skin condition and comparison to similar skin conditions of a patient or of other patients.

17 Claims, 10 Drawing Sheets

SYSTEMS AND METHODS FOR MONITORING THE CONDITION OF THE SKIN

CLAIM FOR PRIORITY

This application claims priority from U.S. Provisional Patent Application Ser. No. 61/345,886, filed on May 18, 2010, and which is incorporated by reference as if fully set forth herein.

BACKGROUND

The subject matter described herein generally relates systems and methods configured for monitoring skin conditions.

The condition of skin is of interest for a variety of reasons, not the least of which are health and cosmetic reasons. As an example of a health concern related to the condition of the skin, the most common type of cancer in the United States is skin cancer. Estimates place the number of new cases of skin cancer for the United States in excess of 1,000,000 per year. The skin is comprised of two main layers, the dermis or lower layer and the epidermis or upper layer. Skin cancer typically originates in the epidermis, which is subject to environmental risk factors (for example, ultraviolet light) thought to initiate cancer formation. The epidermis is comprised of three main types of cells, squamous cells, basal cells and melanocytes.

The most common types of skin cancer are basal cell carcinoma, squamous cell carcinoma, and melanoma. Melanoma is a form of cancer originating in the melanocytes, cells that produce the pigment melanin. Melanoma is the least common of these skin cancers, yet is responsible for approximately three-quarters of skin cancer deaths in the United States. It has been estimated that approximately 2 percent of men and women (or approximately 1 in 53) born today will be diagnosed with melanoma of the skin at some point during their lifetime.

It has been estimated greater than 90 percent of melanomas of the skin can be recognized by visual inspection of the skin. Melanoma of the skin often presents as lesion with a prolonged period of horizontal growth followed by onset of a vertical growth phase and metastasis. Following removal of melanoma tumors less than 1.4 mm in thickness, the probability of recurrence is low (estimated at less than 10 percent).

Given that early stage melanoma can be detected visually and that early removal corresponds to better prognosis, various studies have been conducted and indicate that screening may be effective in terms of early detection. Screening essentially amounts to looking for signs of cancer prior to symptoms appearing. Visual screening for melanoma of the skin often involves inspecting moles (benign (non-cancerous) collections of melanocytes), noting any abnormalities and attempting to monitor any changes over time.

As an example of a cosmetic concern related to the condition of the skin, the appearance of wrinkles is a common skin condition individuals attempt to minimize and/or reverse. Wrinkles are considered a natural part of the aging process. As an individual ages, his or her skin gets thinner and less elastic. This, coupled with exposure to certain environmental factors (such as exposure of skin to sunlight), is thought to contribute to the formation of wrinkles (lines and creases formed in the skin).

The medical, health and cosmetics industries have become involved in wrinkle prevention and management. Individuals dissatisfied with wrinkles now have many treatment options designed to help eliminate or at least diminish the appearance of wrinkles. Such options include for example medications, skin resurfacing techniques, fillers, injectables and even surgery.

BRIEF SUMMARY

Embodiments broadly contemplate systems, methods, apparatuses and program products for identifying, analyzing and/or monitoring the condition of skin. Various embodiments provide for accessing images of the skin, analyzing the characteristics of skin conditions as represented by the images, and providing outputs useful for identifying and/or monitoring conditions of the skin. Certain embodiments provide for automated analysis of skin conditions such as moles or wrinkles. The automated analysis may include for example characterization of a mole's symmetry, border, and/or color. The automated analysis may also include for example comparison of a mole's characteristics to similar moles of a patient or of other patients. The automated analysis may further include characterization of one or more wrinkles as represented in the image. The automated analysis may still further include comparison of the one or more wrinkles to similar wrinkles of a patient or other patients.

In summary, one aspect provides a method comprising: accessing an image representing one or more skin conditions; characterizing the one or more skin conditions represented by the image, said characterizing comprising identifying one or more attributes of the one or more skin conditions represented by the image; and outputting one or more results corresponding to the one or more skin conditions represented by the image.

Another aspect provides an apparatus comprising: one or more processors; and a memory operatively coupled to the one or more processors; wherein, responsive to execution of a program of instructions, the one or more processors are configured to: access an image representing one or more skin conditions; characterize the one or more skin conditions represented by the image, wherein to characterize further comprises identifying one or more attributes of the one or more skin conditions represented by the image; and output one or more results corresponding to the one or more skin conditions represented by the image.

A further aspect provides a computer program product comprising: a computer readable storage medium having a program of instructions embodied therewith, the program of instructions comprising: computer readable program code configured to access an image representing one or more skin conditions; computer readable program code configured to characterize the one or more skin conditions represented by the image, wherein to characterize further comprises identifying one or more attributes of the one or more skin conditions represented by the image; and computer readable program code configured to output one or more results corresponding to the one or more skin conditions represented by the image.

The foregoing is a summary. For a better understanding of example embodiments, together with other and further features and advantages thereof, reference is made to the following description, taken in conjunction with the accompanying drawings, and the scope of the invention will be pointed out in the appended claims.

DETAILED DESCRIPTION

Figure 1:
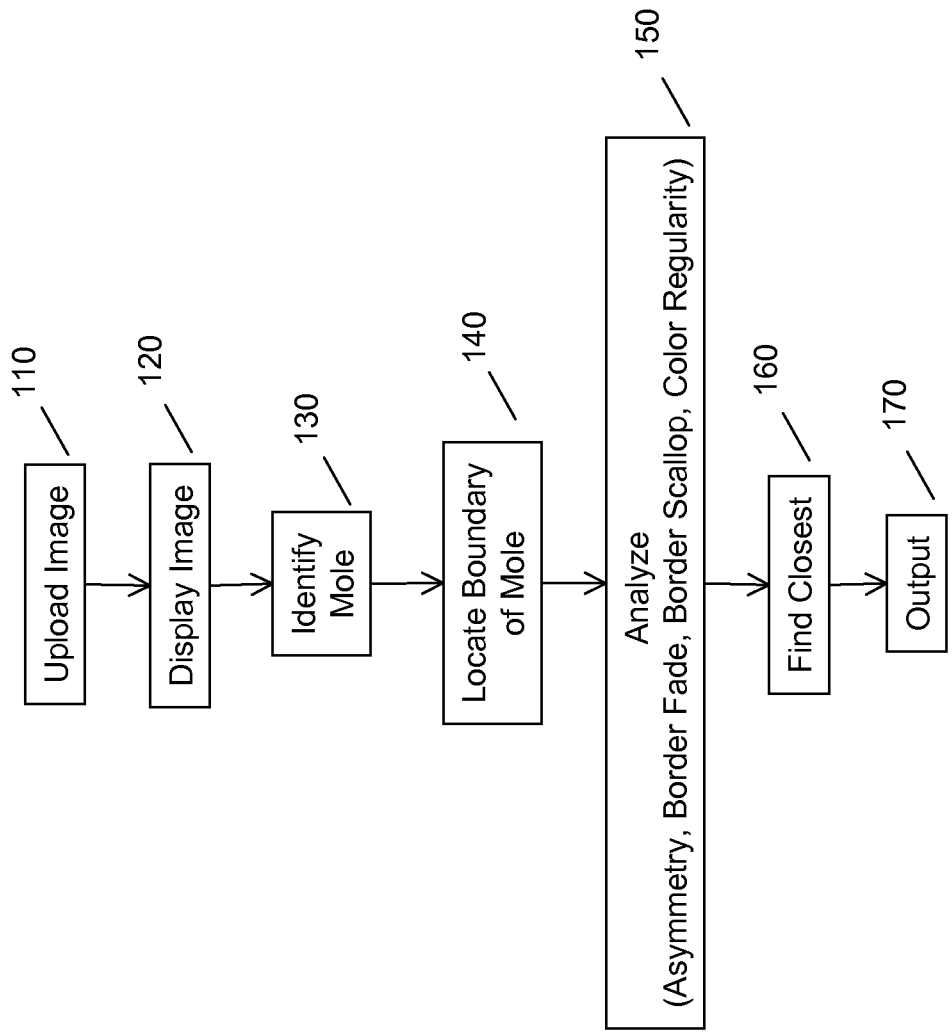
FIG. 1 illustrates an example of characterizing a skin condition.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the invention, as claimed, but is merely representative of certain example embodiments.

Reference throughout this specification to "one embodiment", "an embodiment", "an aspect" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, in the following description, numerous specific details are provided to give a thorough understanding of various example embodiments. One skilled in the relevant art will recognize, however, that various other embodiments can be practiced without one or more of the specific details, or with other methods, components, materials, et cetera. In other instances, well-known structures, materials, or operations are not shown or described in detail to avoid obfuscation.

It will be appreciated by those having ordinary skill in the art that certain example embodiments described herein utilize mole(s) and/or wrinkle(s) as examples of skin condition(s) to be monitored; however, other embodiments are equally applicable to monitoring other skin conditions and skin conditions generally.

Taking skin cancer as a representative context, it can be important to recognize differences between a normal skin condition (for example, a normal mole) and one that is indicative of skin cancer (for example, an abnormal mole). Health care professionals have established guidelines for characterizing moles and other skin conditions, as well as staging the progression of cancers of the skin, and an exhaustive description of these guidelines is not essential for understanding the embodiments described herein. Briefly, a normal mole typically presents as an evenly colored (tan, black, brown, et cetera) spot of less than one-quarter inch on the skin. Normal moles can also be raised or substantially flush with the surface of the skin.

While health care professionals can often readily identify abnormal moles, one key factor in recognizing an abnormal skin condition such as skin cancer is detecting changes in the skin condition, such as changes in shape, size and/or color of a mole over time, as normal moles are typically stable in shape, size, color and/or border/boundary features. Thus, patients and health care professionals are often faced with the challenge of keeping an eye on skin conditions in order to track any changes that take place. Once an abnormal skin condition is recognized, for example if a mole is suspect because it exhibits a change in shape, size, color or the like over time, it can be further scrutinized by a health care professional.

The inventor has recognized that it can be difficult to recognize an abnormal skin condition, particularly for lay individuals. Moreover, it can be difficult to accurately monitor changes in skin conditions, even for health care professionals. This can result from many factors, such as a large number of moles, delay between patient visits, and the like. Thus, screening for abnormal skin conditions can be difficult. Accordingly, the inventor has recognized a need for providing for the effective, easy monitoring of skin conditions.

Various embodiments described herein provide non-limiting examples of systems, methods, apparatuses and program products configured to provide convenient monitoring and analysis of skin conditions. Certain embodiments take as input an image, such as a digital photograph or image of a mole. The image is then analyzed to identify characteristics of the mole, as represented by the image. The analysis can include for example characterization of the size, shape and/or color of the mole. The analysis can further include, for example, comparisons with one or more reference images. The reference image can include for example an earlier photograph of the same mole aligned with the current photograph, and/or stock photographs. Embodiments allow for storing the images and the corresponding analyses in a database. Embodiments provide the images and/or the analyses as output to one or more users. Patients and/or health care professionals can therefore utilize the output for accurate monitoring and/or aid in analysis of skin conditions, such as if and how moles have changed over time, which if any exhibit known abnormal characteristics, and the like.

Accordingly, users can build repositories of images and analyses thereof for convenient review. As will be appreciated by those having ordinary skill in the art, the stored information (for example images, analyses, et cetera) can be supplemented as desired with additional information, such as for example patient historical information, biopsy information, educational information, and the like. Thus, users such as patients and/or health care providers will have additional tools to aid in screening processes for skin conditions.

The illustrated embodiments will be best understood by reference to the figures. The following description is intended only by way of example, and simply describes certain example embodiments.

Referring now to FIG. 1, a user uploads 110 an image to an electronic device. The image, as discussed herein, can include for example a digital photograph of a skin condition, for example a mole. The image is then displayed 120 on a display device operatively connected to the electronic device, such as a monitor. The mole is then identified 130. In order to identify the mole, any one of a number of possibilities may be employed. For example, the system may prompt the user to manually click within the mole's interior using an input device. Alternatively, the system may perform an analysis on the image in order to identify a point within the mole, for example based on characteristics of the pixels of the image. In any event, the mole is identified within the image and analyses such as those described herein are computed.

Once the mole has been identified 130, a boundary (or border or edge) of the mole is identified 140 by the system. As an example, the system may compute the boundary of the mole utilizing circular dynamic programming, as discussed further herein. Once a boundary for the mole has been identified, the system can perform an analysis 150 of the mole. As discussed further herein, the analysis can include one or more of asymmetry analyses, border fade analyses, border scallop analyses, and color regularity analyses.

Once the system has performed the desired analyses 150, the system can access one or more databases having reference information, such as stored reference images of the same or similar moles, and identify 160 a closest (or set of closest) reference image(s) compared to the uploaded image. The result(s) of the analysis and/or the reference image(s) can then be output by the system 170, such as output for display on a display device visible by the user.

Figure 2:
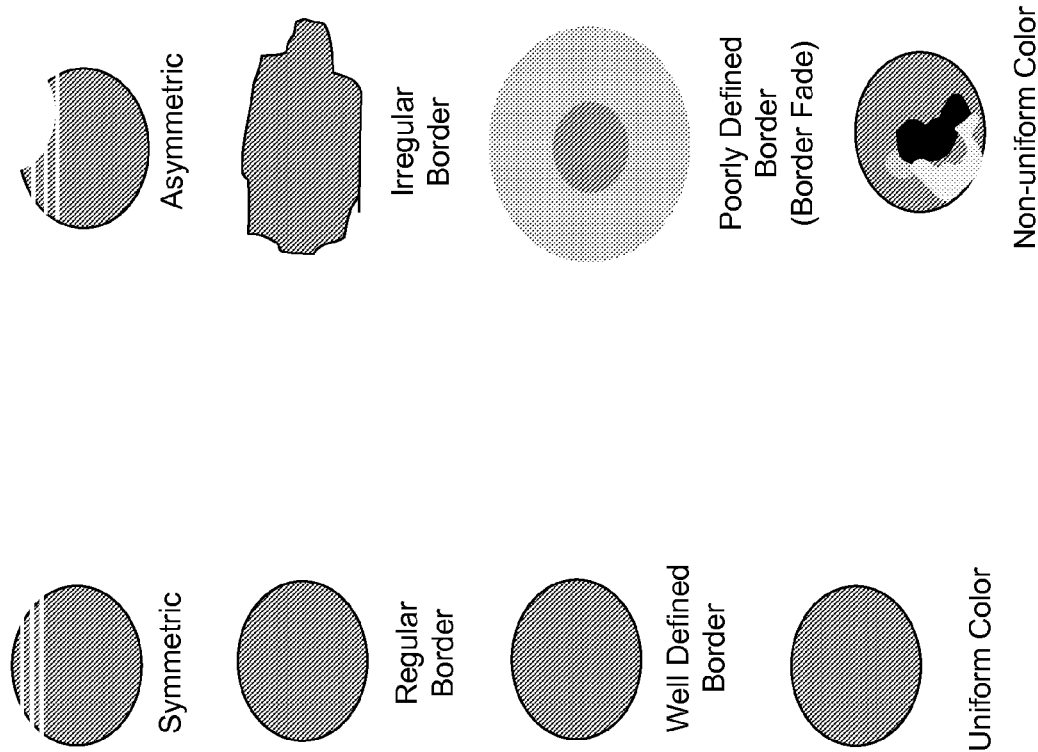
FIG. 2 illustrates examples of moles.

In order to provide some context for the analyses described herein, FIG. 2 provides some non-limiting example illustrations of common or normal moles as compared to irregular or abnormal moles. FIG. 2 illustrates a normal, symmetric mole, having a relatively symmetric boundary, as compared to an asymmetric mole having one or more boundary asymmetries associated therewith. Also illustrated is a normal mole exhibiting a regular border, where the boundary approximates a smooth oval shape, as compared with a mole having an irregular or scalloped border. Further illustrated is a normal mole having a well defined or sharp border, as compared to a mole in which the boundary fades gradually, as per a mole having melanocytes at differing layers below the outermost layer of skin. In addition, a normal mole having essentially a uniform color is illustrated as compared with a mole exhibiting more than one color or an irregular and asymmetric color pattern.

Figure 3B:
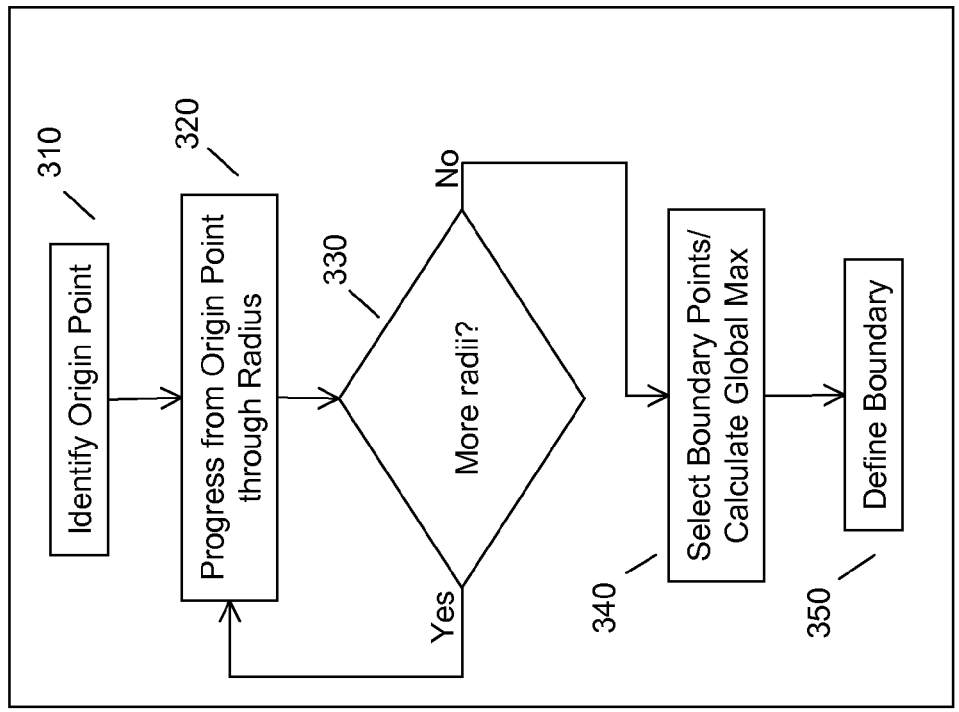
FIGS. 3A and 3B illustrate examples of boundary estimation.
Figure 3A:
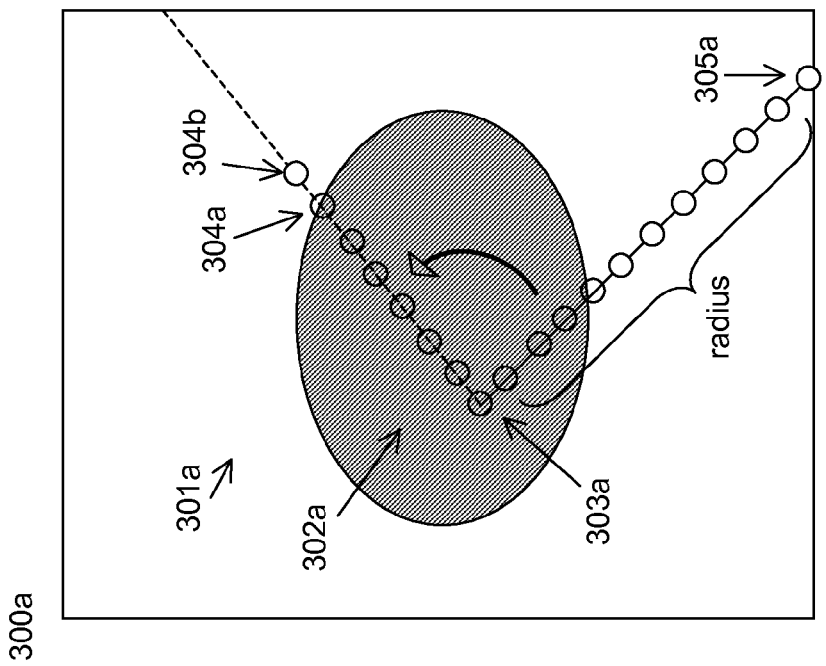

In order to assist in identifying abnormalities such as those illustrated in FIG. 2, and to track changes in moles over time, certain embodiments provide detailed analyses of moles as represented by images. In FIG. 3A-B, an example of boundary identification/definition is illustrated.

As an example of conducting boundary identification/definition, certain embodiments are configured to use dynamic programming in polar coordinates, termed herein as circular dynamic programming. Circular dynamic programming can be characterized essentially as a form of modified dynamic programming. Using dynamic programming, for example in an x, y grid where x is time and y is state, one can find the best state at a given time. In circular dynamic programming, as described herein, the time axis is replaced with an angle, $\theta$, which proceeds in a circle (0-360 degrees) in predefined increments (for example, 1 degree increments); whereas state is considered the potential boundary point for a given $\theta$ along a radius, r.

By way of example, once the mole has been identified, for example via a user clicking on an origin point 303a within the image 301a of the mole 302a, that information can be utilized to identify the boundary of the mole. Starting at the origin 303a (the initial, internal point), radii are sent out from the origin point 303a to the edge of the image 305a. Each circle in FIG. 3A represents for example a point within the image (such as an individual pixel) that is a potential or candidate boundary point. In certain embodiments, each radius progresses pixel-by-pixel from the origin point 303a to the edge of the image, one radius being defined per degree. For each pixel, features are accessible to the system, such as color level or intensity, and the system is configured to gather and store this feature information for the points. This builds up a sequence of points and features thereof within the image, each point being a candidate boundary point, with a sequence of points actually defining the boundary of the mole in the image.

In order to identify a candidate point as a boundary point, after one or more features of the points has been identified, a global maximum reward can be calculated for selecting candidate boundary points as the actual boundary points defining a border of the mole. The following is a non-limiting example of boundary point identification and boundary definition.

By way of example, a feature of a candidate point that can be utilized for determining if it is a boundary point includes a measurable feature of the image such as color level or intensity of a pixel. A candidate boundary point can be evaluated based on this measurable feature by determining a difference value, as for example by comparing the candidate point with surrounding points of the particular radius. A maximal difference value for a measurable feature between two points on a particular radius is indicative of a boundary point. For example, a color transition is illustrated between points 304a and 304b, where the color of 304a is more intense/at a higher level than that of 304b. This is indicative of 304a as being a boundary point.

Once features have been identified for each point of each radius, a global maximum reward can be calculated for choosing the best boundary points, taking into account a discontinuity measure (to be minimized). For example, the discontinuity measure can be defined as a difference between the distance from the origin to a given boundary point for a radius as compared with the distance from the origin to a boundary point of an immediately surrounding radius. A penalty value can be enforced for jumps in distance as part of the overall boundary definition calculation. Thus, discontinuity in lengths between origin and boundary can be minimized. Once all the candidate points have been evaluated, and all candidate points have been compared, a trace back process can be completed for the identified best boundary for the mole represented within the image.

By way of further refinement, the following equation represents a global reward to be maximized for placing a boundary or border point at a particular candidate point (r, $\theta$):

$$C(R,\theta)=\max\{C(r,\theta-1)-\text{dist}(r,R)\}$$

where $C(r, \theta-1)$ is a measure of the gradient (for example, color intensity difference between points) and dist(r, R) is a measure of the discontinuity (for example, a difference in lengths from origin to boundary points for radii).

FIG. 3B illustrates an example method for defining boundary points and establishing a border for a mole using circular dynamic programming. As discussed herein, the origin or internal point is identified 310. The system will gather one or more features for the origin point and proceed through the points of a given radius 320, gathering features of the points of the radius. As discussed herein, this procedure may be an exhaustive process, for example by defining the radius of points as extending to the edge of the image such that the process continues through all points to the edge of the image. Thereafter, it is determined 330 if there are more radii, in which case the process can be repeated for the next radius. If there are no more radii, candidate boundary points are selected and the global maximum calculated 340 for a border using the candidate boundary points. The boundary points giving the global maximum reward are used to define the boundary of the mole 350. Note that the number of points analyzed and/or the number of radii analyzed can be modulated as desired, for example based on the resolution of the image, the processing power of the given system, et cetera.

Certain embodiments are configured to provide detailed analysis of one or more features of a skin condition, such as a mole, based in part on the boundary or border derived from the image. For example, using the information derived from the image of the skin condition, such as features of pixels gathered from the image, certain embodiments are configured to provide analysis of symmetry measures, such as radius asymmetry and color asymmetry.

Figure 4B:
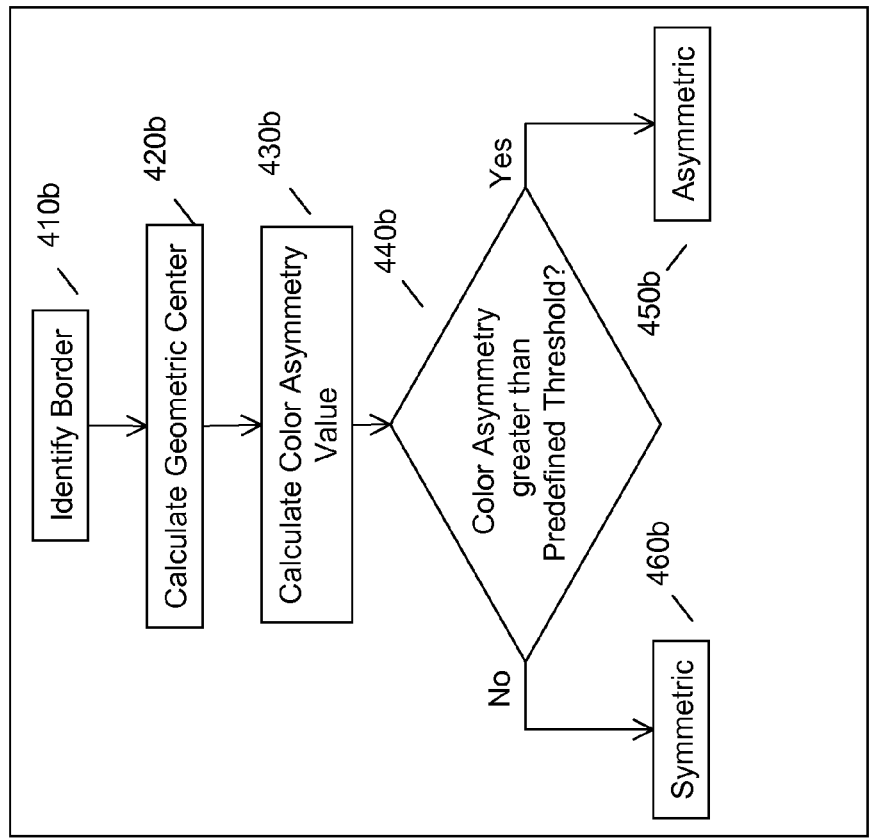
FIGS. 4A and 4B illustrate examples of identifying asymmetry of a skin condition.
Figure 4A:
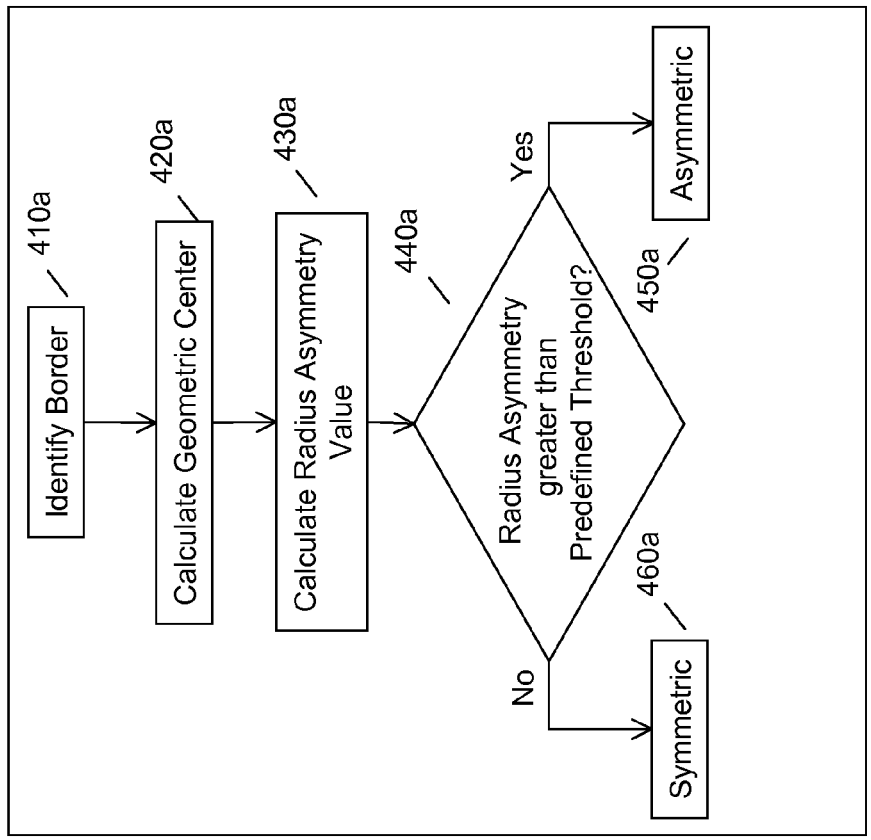

Turning to FIG. 4A, an example of identifying and analyzing radius asymmetry is illustrated. The general idea behind a radius asymmetry analysis is to determine if the mole is symmetric in shape or is asymmetric in shape, and to distinguish between these. As discussed herein, an internal origin point of the mole can be identified, either by a user clicking on an internal point within the mole or by having the system automatically calculate an internal point. This internal point is useful, for example as an origin point for an analysis to identify boundary points and defining a border of the mole, as described herein. However, to conduct an asymmetry analysis of the mole, it is useful to identify the geometric center of the mole (as represented in the image) using the system. This provides a more precise point of reference for determining geometric asymmetry.

Accordingly, at 410a the system identifies the border of the mole, as discussed herein. As will be understood, the geometric center of the mole can be identified using the border 420a (for example, taking the mean of the points which comprise the border). Thereafter, radii from the geometric center can be calculated. A radius asymmetry can then be calculated 430a for the mole. The radius asymmetry value can be calculated in a variety of ways.

For example, radius asymmetry can be defined as proportional to a count of the number of points at a given $(r, \theta)$ and $(r, \theta+180)$ falling on opposite sides of the boundary. This could be for example in the form of a calculated percentage, that is the number of symmetric observations divided by the number of asymmetric observations. The calculated asymmetry value determined using the geometric center is compared to a predefined threshold value 440a. If the value for the radius asymmetry is greater than the predefined threshold value, the mole can be reported as being of asymmetric shape 450a. Otherwise, the mole can be reported as symmetric in shape 460a. Alternatively, a degree of asymmetry can be reported, which is proportional to the percentage of values that exceed the predefined threshold. This degree may be mapped to a discrete scale, for example 0, 1, 2, 3, 4, or 5 out of 5.

Referring to FIG. 4B, color asymmetry can similarly be calculated for a mole. The general idea behind a color asymmetry analysis is to determine if a mole's colors are symmetric at points throughout the mole, or if the mole exhibits asymmetric color properties, and to distinguish between these. With the border of the mole identified 410b, the geometric center is again calculated 420b. A value representing color asymmetry is calculated 430b. As with radius or shape asymmetry, a variety of methodologies can be employed to calculate color asymmetry.

For example, color asymmetry can be defined as proportional to the sum of difference in grey level value of pixels at $(r, \theta)$ and $(r, \theta+180)$ of points within the interior (as defined by the border). This could be for example in the form of a calculated average (the average difference in absolute values of grey pixel levels for symmetrically located points within the interior). Once a color asymmetry value has been defined for the mole, the value can again be compared to a predefined threshold 440b. If the color asymmetry value is greater than the predefined threshold, the mole can be reported as asymmetric in color at 450b. Otherwise, the mole can be reported as being symmetric in color 460b. Alternatively, a degree of asymmetry can be reported, which is proportional to the percentage of values that exceed the predefined threshold. This degree may be mapped to a discrete scale, for example 0, 1, 2, 3, 4, or 5 out of 5.

Figure 5:
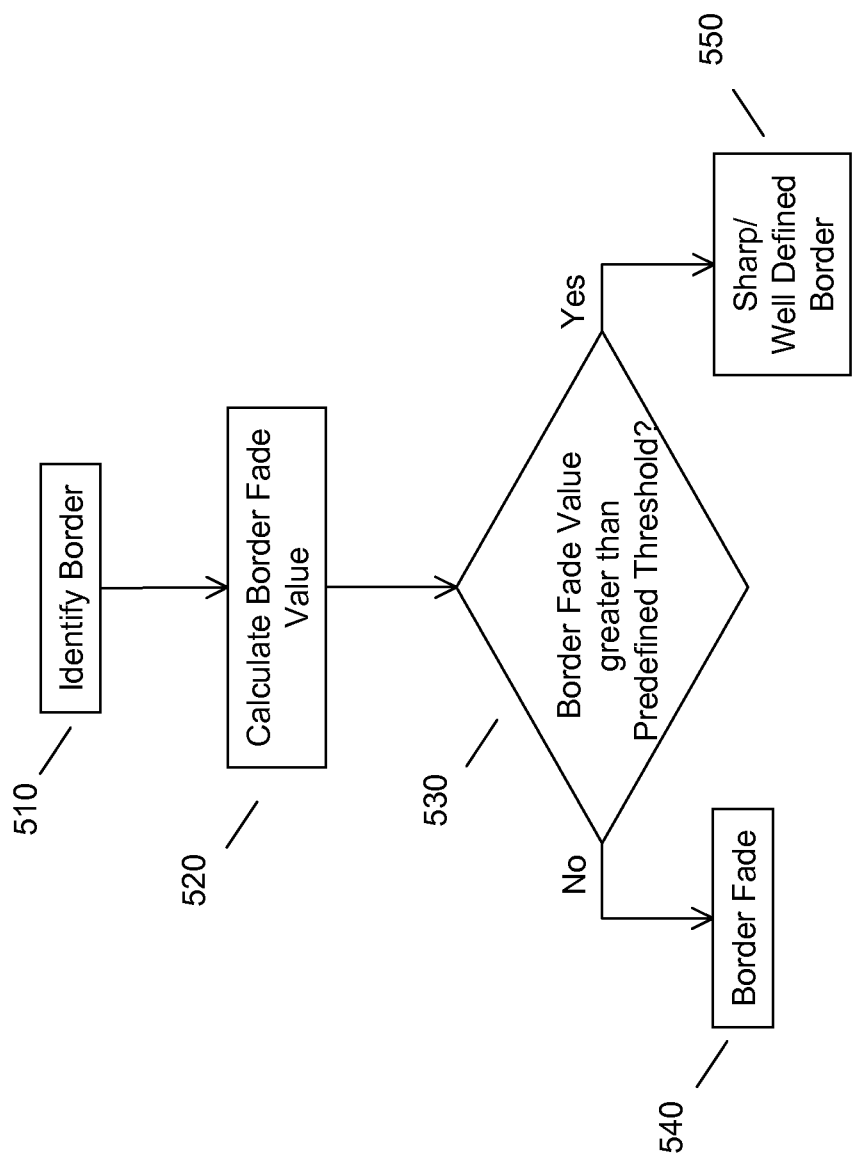
FIG. 5 illustrates an example of identifying border fade.

Turning to FIG. 5, certain embodiments are configured to calculate border fade. The general idea behind a border fade analysis is to determine if the border is well defined, that is sharp, or is ill defined and difficult to identify, and to distinguish between these. As an example border fade analysis, the border is first identified for the mole 510. Thereafter, a border fade value is calculated 520. As an example of a border fade value calculation, the differences in pixel grey level value at $\theta=0:360$ for points on the interior and exterior of the border can be accumulated. The accumulation can take any of a variety of forms, such as determining a percentage of points that exhibit greater than a threshold amount of grey level value difference. The border fade value can then be compared to a predefined threshold value 530. If the difference in the accumulated grey pixel level values is greater than a threshold, the border can be reported as sharp or well defined 550 (that is, the points on the interior and exterior of the border exhibit a large difference in color). Otherwise, the border can be reported as exhibiting border fade 540. Alternatively, the degree of border fade may be reported, and may optionally be quantized as in the symmetry calculation(s).

Figure 6:
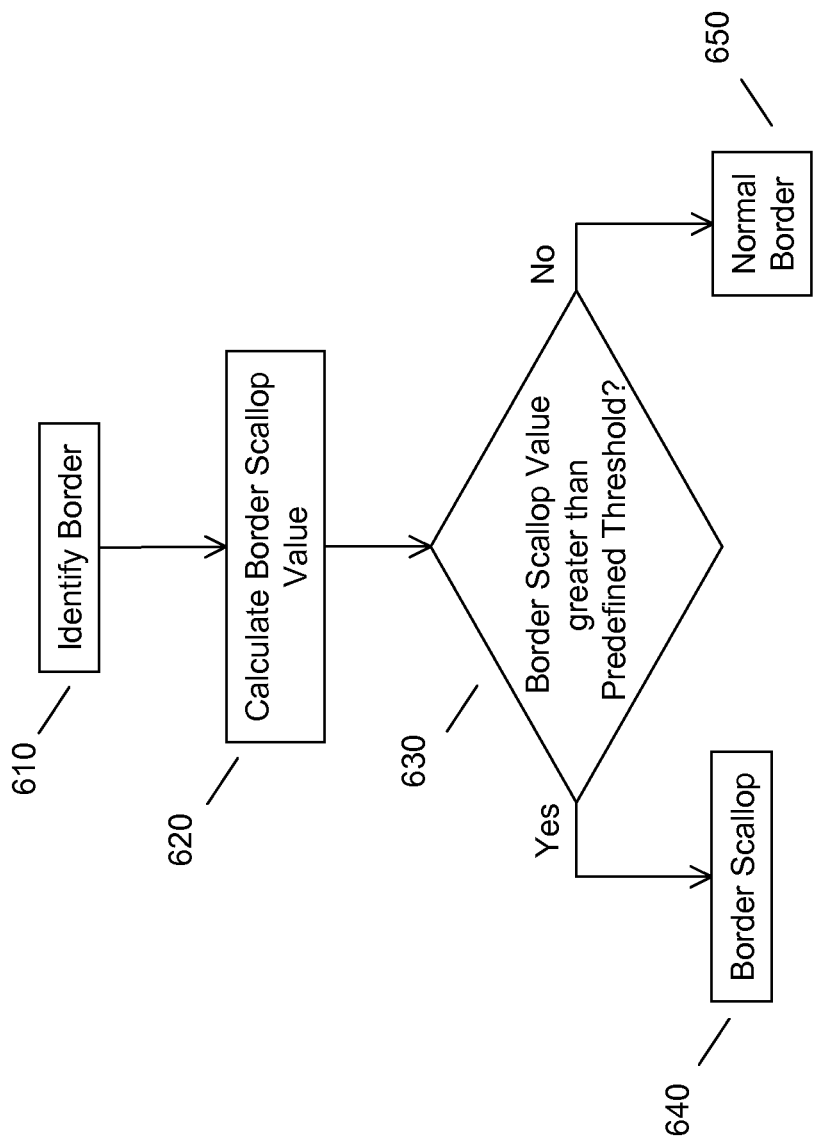
FIG. 6 illustrates an example of identifying border scallop.

Turning to FIG. 6, certain embodiments are configured to calculate border scallop. The general idea behind a border scallop analysis is to determine if the border is regular, that is smooth, or is scalloped or wavy, and to distinguish between these. As an example border scallop analysis, the border is first identified 610. A border scallop value is then determined 620. The border scallop value can be calculated or determined in a variety of ways. For example, a best fit shape (for example, an oval) can be determined (for example, using a least squares computation) for the border defining the boundary of the mole. Using this best fit to the border of the mole, the differences (for example, pixel by pixel) can be determined between the best-fit and the actual border, as determined using methods described herein. The differences between the best-fit (which is a non-scalloped shape) and the actual border can be utilized as a border scallop value. The differences can be mapped into a variety of border scallop scores (such as a scale from 1 to 10). The border scallop score can either be directly reported (for example as a 1 to 10 score) or compared to a predefined threshold value 630. If the border scallop value exceeds the predefined threshold, the mole can be reported as exhibiting border scallop 640. Otherwise, the mole can be reported as exhibiting a normal border 650. Alternatively, the degree of border scallop may be reported by reporting the percentage of points whose scallop value exceeds a predefined threshold. This value may be quantized and mapped, for example to a scale of 0 to 5.

Figure 7:
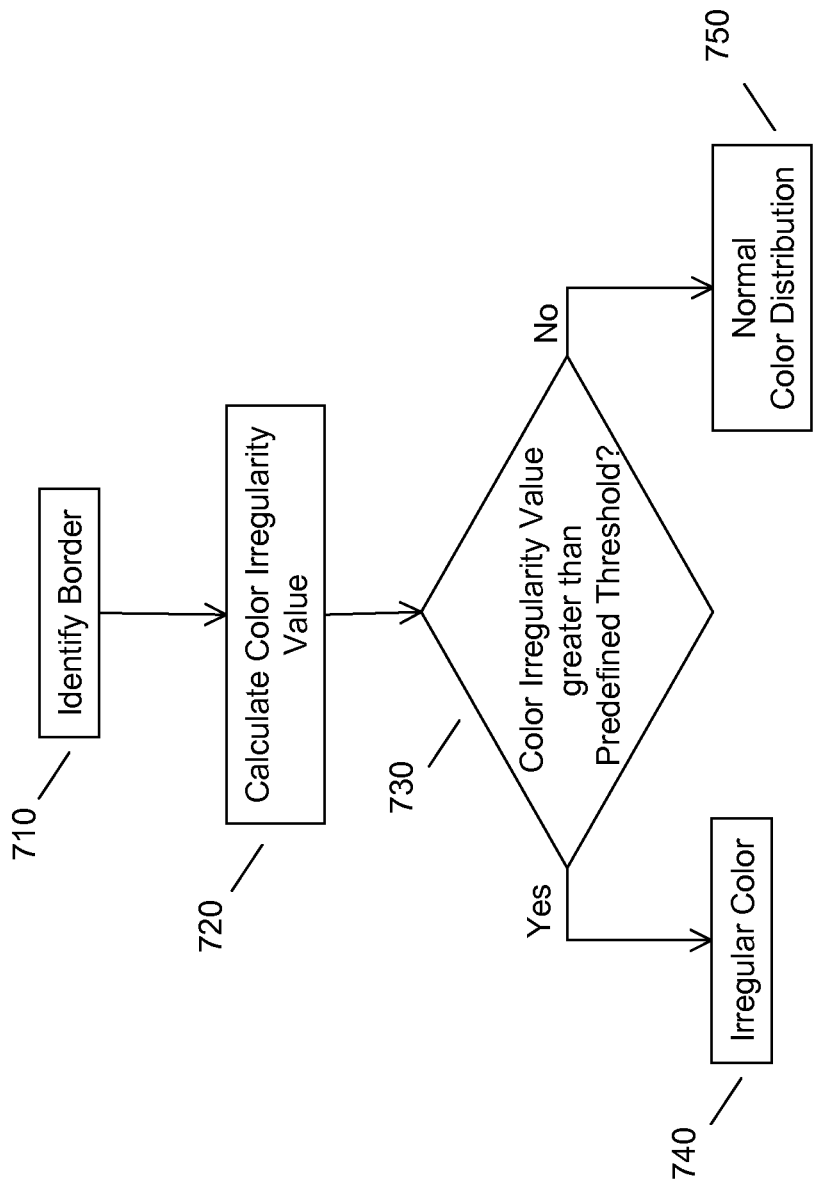
FIG. 7 illustrates an example of identifying color irregularity.

Turning to FIG. 7, certain embodiments are configured to analyze color irregularity. The general idea behind a color irregularity analysis is to determine if the color of a mole is regular throughout, that is solid or consistent throughout, or is variable, and to distinguish between these. This differs from color asymmetry because a mole may be symmetric in color, while still exhibiting color irregularity (for example, exhibit different colors (irregular) in a symmetric way (exhibit color symmetry)).

As an example of a color irregularity analysis, the border of the mole is first identified 710. Thereafter a color irregularity score is calculated 720. A color irregularity score can be calculated in a variety of ways. For example, a histogram of colors within the border can be computed. Thereafter, entropy of the distribution of colors can be computed as a color irregularity value, where the entropy value of the distribution of colors increases with increasing colors exhibited in the mole. For example, for a grey level image, the grey level values are between 0 and 255. A histogram can be computed indicating the number of pixels exhibiting each value. This yields a discrete distribution from 0 to 255 that can be normalized (for example, using the total number of pixels within the interior) and characterized. The entropy value can be mapped to a scaled score (such as 1 to 10) or can be compared with a predefined threshold value 730. If the color irregularity value exceeds the predefined threshold value, the mole can be reported as exhibiting irregular color 740. Otherwise, the mole can be reported as having a normal color distribution 750. Alternatively, the degree of color irregularity may be reported as the percentage of values which exceed the predefined threshold. The degree of color irregularity may be quantized and mapped, for example to a scale of 0 to 5.

Figure 8:
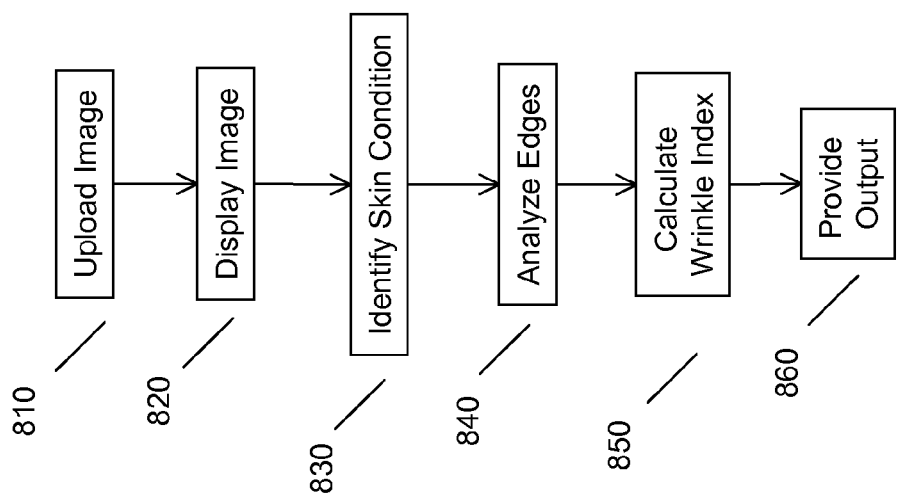
FIG. 8 illustrates an example of characterizing a skin condition.

Referring to FIG. 8, in addition to monitoring and analyzing skin conditions such as moles, other embodiments provide convenient monitoring and analysis of other skin conditions, such as wrinkles. Thus, certain embodiments take as input an image, such as a digital photograph (image) of a portion of skin containing one or more wrinkles. The image is then analyzed to identify characteristics of the wrinkles, as represented by the image.

The analysis can include for example characterization of the edges (representing the wrinkles) in the image. The analysis can include for example automated finding of edges in the image by calculating the gradient of the image and searching for local maxima in the magnitude of the gradient. The intensity of all edges falling in a given area (for example, user selected or marked area) whose strength is greater than a threshold are summed to give a "wrinkle index", which is for example a scaled score corresponding to a value representing the strength of the edges in the marked area. The analysis can further include, for example, comparisons with one or more reference images of wrinkles. The reference image can include for example an earlier photograph/image of the same area aligned with the current image, and/or stock images. As with the examples described in connection with moles, embodiments allow for storing the images and the corresponding analyses in a database. Embodiments provide the images and/or the analyses as output to one or more users.

As a non-limiting example, an individual can complete a wrinkle analysis before and after undergoing a wrinkle treatment in order to test the efficacy of the treatment. If the wrinkle treatment was effective, the wrinkle index should decrease and/or the best match reference image(s) should appear less wrinkled than the previous best match.

Edge detection is a fundamental tool in computer vision and image processing. Various algorithms have been devised for detecting edges in photographs; most of them can be categorized as either search-based or zero-crossing based. The search-based methods detect edges by first computing a measure of edge strength, such as the gradient magnitude, and then searching for local maxima of the gradient magnitude. The zero-crossing based methods look for zero crossings in a second-order derivative computed from the image. Wrinkle analysis can be performed by embodiments using any suitable edge detection method.

By way of further example, an individual can take a digital image of the skin. A user can then upload the image 810 to the system. The image can then be displayed 820 on a display device to allow the user to identify the skin condition 930. For example, the user can use an input device (such as a mouse) to mark area(s) of concern. The system then analyses the skin condition 840 represented by the marked area(s) to provide a wrinkle index. The wrinkle index can be calculated in a variety of ways. For example, the system finds edges in the marked area(s) of the image by applying an edge detection algorithm. The intensity of edges falling in the marked area whose strength is greater than a threshold can be summed to give the wrinkle index. The analysis of the marked areas representing the identified skin condition can then be provided as output 850 to the user.

The user is able to compare the current wrinkle index to the index of a reference image or of a set of images in a database. The closest wrinkle index(es) in the database, as determined for example by using Euclidean distance, is calculated and the associated reference image(s) is displayed. Thus, similar to the example skin condition analyses described in connection with moles, patients and/or health care professionals can utilize the output for accurate monitoring and/or aid in analysis of skin conditions, such as if and how a wrinkle treatment has changed the skin condition, the development of wrinkles over time, and the like.

Figure 9:
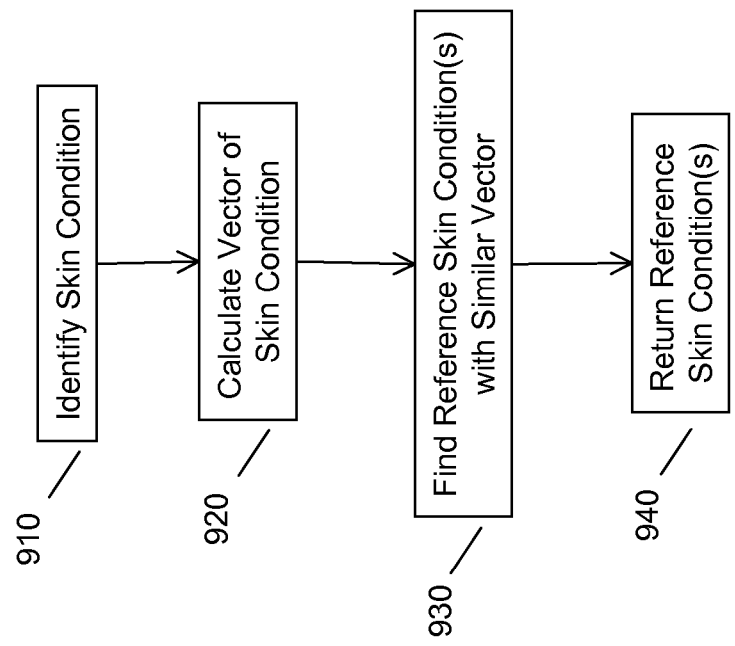
FIG. 9 illustrates an example of finding reference skin condition(s).

Turning to FIG. 9, certain embodiments are configured to calculate a vector representing a skin condition using one or more of the analyses. As just one example, a four-dimensional "ABBC" (asymmetry, border fade, border scallop, and color) vector can be computed using the analyses described herein. The vector represents a comparable definition of the skin condition based on the results of one or more of the analyses. For example, the vector can comprise real values between 1 and 10 for each score included in the vector. Once the vector has been calculated for a particular skin condition, one or more databases can be accessed to find skin conditions with similar vectors.

As illustrated in FIG. 9, a skin condition can be identified 910. The vector of the skin condition can be calculated 920. One or more reference skin conditions (as for example represented by images having vectors assigned thereto) can be identified 930, for example by comparing the Euclidean distance between the current mole's vector and the vectors of moles in the one or more databases. Thereafter, the one or more reference skin conditions can be returned, for example for review by a user 940.

It will be readily understood that certain embodiments can be implemented using any of a wide variety of devices. For example, a server hosting a web site may be linked to a client device, wherein the client device is used by a user to upload images and the server, remotely located and connected to the client device via the Internet, is used to perform the analyses and return result(s) to the user. In the alternative, a stand-alone device could be utilized.

Figure 10:
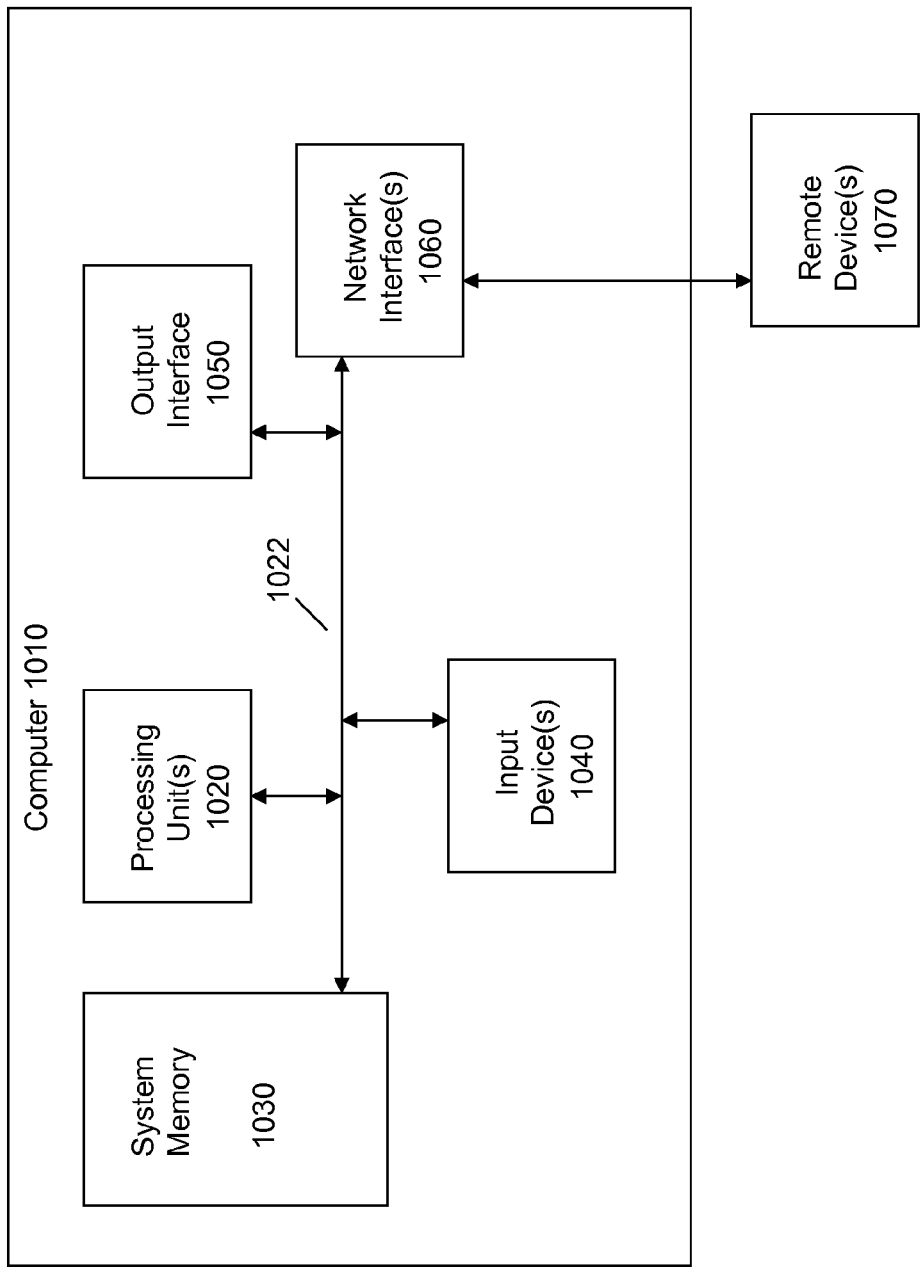
FIG. 10 illustrates an example computer.

FIG. 10 illustrates an example device that may be used in implementing one or more embodiments in the form of a computer 1010. In this regard, the computer 1010 may execute program instructions configured to perform the analyses discussed herein and perform other functionality of a skin analysis and tracking system, as described herein.

Components of computer 1010 may include, but are not limited to, a processing unit 1020, a system memory 1030, and a system bus 1022 that couples various system components including the system memory 1030 to the processing unit 1020. Computer 1010 may include or have access to a variety of computer readable media. The system memory 1030 may include computer readable storage media in the form of volatile and/or nonvolatile memory such as read only memory (ROM) and/or random access memory (RAM). By way of example, and not limitation, system memory 1030 may also include an operating system, application programs, other program modules, and program data.

A user can interface with the computer 1010 (for example, enter commands and information, such as upload one or more images) through input devices 1040. A monitor or other type of device can also be connected to the system bus 1022 via an interface, such as an output interface 1050. In addition to a monitor, computers may also include other peripheral output devices. The computer 1010 may operate in a networked or distributed environment using logical connections to one or more other remote computers. The logical connections may include a network, such local area network (LAN) or a wide area network (WAN), but may also include other networks/buses.

It should be noted as well that certain embodiments may be implemented as a system, method or computer program product. Accordingly, aspects of the invention may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples of the computer readable storage medium would include the following a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the invention may be written in any combination of one or more programming languages (including an object oriented programming language such as Java™, Smalltalk, C++ or the like and conventional procedural programming languages, such as the "C" programming language or similar programming languages). The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the invention are described herein with reference to flowchart illustrations and/or block diagrams of methods, apparatuses, systems and computer program products according to embodiments of the invention. It will be understood that block(s) of the flowchart illustrations and/or block diagrams, and combinations of block(s) in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, implement the functions/acts specified in the flowchart and/or block diagram block(s).

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block(s).

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block(s).

This disclosure has been presented for purposes of illustration and description but is not intended to be exhaustive or limiting. Many modifications and variations will be apparent to those of ordinary skill in the art. The embodiments were chosen and described in order to explain principles and practical application, and to enable others of ordinary skill in the art to understand the disclosure for various embodiments with various modifications as are suited to the particular use contemplated.

Although illustrative embodiments have been described herein with reference to the accompanying drawings, it is to be understood that the embodiments are not limited to those precise embodiments, and that various other changes and modifications may be affected therein by one skilled in the art without departing from the scope or spirit of the disclosure.

What is claimed is:
1. A method comprising:
  accessing an image stored in a memory representing one or more skin conditions submitted by a user;
  identifying, by at least one device processor, any internal portion of a mole represented the image;
  utilizing circular dynamic programming to identify a border of the mole via analyzing, by the at least one device processor, pixel data in radii of a circle of predefined increments from an origin point corresponding to any internal portion of the mole to an edge of the image;
  wherein identifying the mole border represented by the image utilizing circular dynamic programming further comprises:
  for pixel data in a radius, determining a difference value for a first potential boundary point with one or more surrounding points of the radius;

choosing a candidate boundary point in the radius as the pixel in the radius having the maximal difference value based on the determining;

iterating the determining for each radius in 360 degrees; and calculating a global maximum reward to refine candidate boundary points of the radii, wherein the global maximum reward is based on discontinuity between radius length from origin for proximately located radii;

characterizing, by the at least one device processor, the one or more skin conditions represented by the image, said characterizing comprising identifying one or more attributes of the mole using pixel data within the mole border; and outputting, by the at least one device processor, one or more results corresponding to the one or more skin conditions represented by the image.

2. The method according to claim 1, wherein the one or more skin conditions comprise one or more moles.

3. The method according to claim 1, further comprising identifying an internal portion of a mole represented by the image via receiving user input corresponding to selection of the internal portion.

4. The method according to claim 1, wherein identifying one or more attributes comprises identifying one or more of an amount of asymmetry of a mole represented by the image, an amount of border fade of a mole represented by the image, an amount of border scallop of a mole represented by the image, and an amount of color regularity of a mole represented by the image.

5. The method according to claim 4, wherein:
an amount of asymmetry of a mole represented by the image comprises one or more of an amount of radius asymmetry and an amount of color asymmetry.

6. The method according to claim 4, wherein an amount of border fade of a mole represented by the image is calculated utilizing an accumulated difference of pixel grey level values.

7. The method according to claim 4, wherein an amount of border scallop of a mole represented by the image is calculated utilizing a best-fit shape to the border and calculating a difference value representing a difference between the best-fit shape and the border.

8. The method of claim 1, wherein the characterizing one or more attributes of the mole using pixel data within the mole border concludes without reference to another mole identified within the image.

9. The method of claim 1, wherein a geometric center of the mole is not determined.

10. The method of claim 1, wherein the characterizing comprises characterizing using only pixels of a single mole within the image.

11. An apparatus comprising:
one or more device processors; and
a memory operatively coupled to the one or more device processors;
wherein, responsive to execution of a program of instructions, the one or more device processors are configured to:
access an image representing one or more skin conditions submitted by a user;
identify any internal portion of a mole represented the image;
utilize circular dynamic programming to identify a border of the mole via analyzing pixel data in radii of a circle of predefined increments from an origin point corresponding to any internal portion of the mole to an edge of the image;

wherein to utilize circular dynamic programming to identify the mole border represented by the image further comprises:

for pixel data in a radius, determining a difference value for a first potential boundary point with one or more surrounding points of the radius;

choosing a candidate boundary point in the radius as the pixel in the radius having the maximal difference value based on the determining;

iterating the determining for each radius in 360 degrees; and calculating a global maximum reward to refine candidate boundary points of the radii, wherein the global maximum reward is based on discontinuity between radius length from origin for proximately located radii;

characterize the one or more skin conditions represented by the image, wherein to characterize further comprises identifying one or more attributes of the mole using pixel data within the mole border; and output one or more results corresponding to the one or more skin conditions represented by the image.

12. The apparatus according to claim 11, wherein the one or more skin conditions comprise one or more moles.

13. The apparatus according to claim 12, wherein, responsive to execution of a program of instructions, the one or more processors are configured to identify an internal portion of a mole represented by the image via receiving user input corresponding to selection of the internal portion.

14. The apparatus according to claim 11, wherein identifying one or more attributes comprises identifying one or more of an amount of asymmetry of a mole represented by the image, an amount of border fade of a mole represented by the image, an amount of border scallop of a mole represented by the image, and an amount of color regularity of a mole represented by the image.

15. The apparatus according to claim 14, wherein:
an amount of asymmetry of a mole represented by the image comprises one or more of an amount of radius asymmetry and an amount of color asymmetry.

16. The apparatus according to claim 14, wherein an amount of border fade of a mole represented by the image is calculated utilizing an accumulated difference of pixel grey level values; and wherein an amount of border scallop of a mole represented by the image is calculated utilizing a best-fit shape to the border and calculating a difference value representing a difference between the best-fit shape and the border.

17. A computer program product comprising:
a non-transitory computer readable storage medium having a program of instructions embodied therewith, the program of instructions comprising:
computer readable program code configured to access an image representing one or more skin conditions submitted by a user;
computer readable program code configured to identify any internal portion of a mole represented the image;
computer readable program code configured to utilize circular dynamic programming to identify a border of the mole via analyzing pixel data in radii of a circle of predefined increments from an origin point corresponding to any internal portion of the mole to an edge of the image;
wherein to utilize circular dynamic programming to identify the mole border represented by the image further comprises:
for pixel data in a radius, determining a difference value for a first potential boundary point with one or more surrounding points of the radius;

choosing a candidate boundary point in the radius as the pixel in the radius having the maximal difference value based on the determining;

iterating the determining for each radius in 360 degrees; and calculating a global maximum reward to refine candidate boundary points of the radii, wherein the global maximum reward is based on discontinuity between radius length from origin for proximately located radii;

computer readable program code configured to characterize the one or more skin conditions represented by the image, wherein to characterize further comprises identifying one or more attributes of the mole using pixel data within the mole border; and computer readable program code configured to output one or more results corresponding to the one or more skin conditions represented by the image.

* * * * *